United States Patent [19]

Purohit et al.

[11] Patent Number: 5,550,040
[45] Date of Patent: Aug. 27, 1996

[54] METHOD, REAGENTS AND KITS FOR THE DETECTION OF *NEISSERIA GONORRHOEAE*

[75] Inventors: Ashok P. Purohit, Sommerville; Sheryl B. Silver, Paramus, both of N.J.

[73] Assignee: Hoffman-La Roche Inc., Nutley, N.J.

[21] Appl. No.: 214,861

[22] Filed: Mar. 17, 1994

Related U.S. Application Data

[63] Continuation-in-part of Ser. No. 82,851, Jun. 23, 1993, abandoned.

[51] Int. Cl.$^6$ ............. C12P 19/34; C07H 21/02; C07H 21/04; C12N 15/00
[52] U.S. Cl. ............. 435/91.2; 435/6; 435/91.1; 435/183; 435/810; 536/24.32; 536/24.33; 536/25.3; 935/76; 935/77; 935/78
[58] Field of Search ............. 435/6, 91.1, 91.2, 435/183, 810; 536/23.1, 23.7, 24.32, 24.33, 25.3; 935/1, 5, 8, 76, 77, 78

[56] References Cited

U.S. PATENT DOCUMENTS

| | | | |
|---|---|---|---|
| 4,683,195 | 7/1987 | Mullis et al. | 435/6 |
| 4,755,458 | 7/1988 | Rabbani et al. | 435/7 |
| 4,767,699 | 8/1988 | Vary et al. | 435/6 |
| 4,900,659 | 2/1990 | Lo et al. | 435/6 |
| 5,047,523 | 9/1991 | Woods et al. | 536/27 |
| 5,075,216 | 12/1991 | Innis et al. | 435/6 |
| 5,132,207 | 7/1992 | Kohne et al. | 435/6 |
| 5,162,199 | 11/1992 | Stern et al. | 435/6 |
| 5,232,829 | 8/1993 | Longiaru et al. | 435/6 |
| 5,256,536 | 10/1993 | Miyada et al. | 435/6 |
| 5,333,675 | 8/1994 | Mullis et al. | 165/12 |
| 5,378,606 | 1/1995 | Stern et al. | 435/6 |
| 5,432,271 | 7/1995 | Barns et al. | 536/24.32 |

FOREIGN PATENT DOCUMENTS

| | | | |
|---|---|---|---|
| 237737 | 1/1987 | European Pat. Off. | C12Q 1/68 |
| WO88/03957 | 2/1988 | WIPO | C12Q 1/68 |

OTHER PUBLICATIONS

Ritchot, et al., Gene, 86:103–106(1990) "DNA Mthylation in *Neisseria gonorrhoeae* and other Neisseriae".

Born, et al., Molecular and Cellular Probes 5:327–335 (1991) "A DNA Sequence for the Discrimination of *Neisseria gonorrhoeae* from other Neisseria Species".

*Primary Examiner*—W. Gary Jones
*Assistant Examiner*—Bradley L. Sisson
*Attorney, Agent, or Firm*—George M. Gould; William H. Epstein; Patricia S. Rocha-Tramaloni

[57] ABSTRACT

Methods, reagents and kits are provided for simultaneously amplifying and detecting polynucleotide sequences in bacteria causing *Neisseria gonorrhoeae* and/or *Chlamydia trachomatis* using primers and probes specific for each bacterial species.

8 Claims, 3 Drawing Sheets

N. GONORRHOEAE PRIMERS AND PROBE

PRIMER SS01      5'                                    3'
                 TAG CCA CGT TTA TCG TCG TAT GC
                         (SEQ ID NO:1)

PRIMER SS02      5'                                    3'
                 AAC AGC ATT ACC AAT CTG GCG AC
                         (SEQ ID NO:2)

PROBE SS06-T5    5'                                    3'
                 GCG GTT CAG GGA AGT GAT AG
                         (SEQ ID NO:3)

AMPLIFIED TARGET SEQUENCE = 201 bp

FIG. 1

C. TRACHOMATIS PRIMERS AND PROBE

PRIMER CP24
5'                              3'
GGG ATT CCT GTA ACA ACA AGT CAG G
(SEQ ID NO:4)

PRIMER CP27
5'                              3'
CCT CTT CCC CAG AAC AAT AAG AAC AC
(SEQ ID NO:5)

PROBE CP35
5'                              3'
CAT AGC ACT ATA GAA CTC TGC AAG CC
(SEQ ID NO:6)

AMPLIFIED TARGET SEQUENCE = 207 bp

*FIG. 2*

METHOD, REAGENTS AND KITS FOR THE DETECTION OF *NEISSERIA GONORRHOEAE*

This application is a continuation-in-part application of U.S. Ser. No. 08/082,851, filed on June 23, 1993, now abandoned.

TECHNICAL FIELD

The present invention relates generally to methods and reagents for identifying and detecting the bacterium *Neisseria gonorrhoeae* ("*N. gonorrhoeae*"), the causative agent of gonorrhea.

BACKGROUND OF THE INVENTION

Gonorrhea is one of the most commonly reported bacterial infection in the United States. Over 3 milion cases are reported annually. See Morello et al., "Neisseria and Branhamella", *Manual of Clinical Microbiology* (5th Ed. 1991), pp. 258–276.

In order to treat successfully a disease caused by a bacterium, for example *Neisseria gonorrhoeae*, the rapid and accurate detection and identification of the disease-causing bacterium is required. The detection and identification has traditionally been accomplished by pure culture isolation and determination procedures that make use of knowledge of specimen source, growth requirements, visible (colony) growth features, microscopic morphology, staining reactions, and biochemical characteristics.

Conventional methods of detecting and identifying the causative agent of gonorrhea, *N. gonorrhoeae*, include the Gram-stain, culturing on selective agar medium, and cytochrome oxidase and carbohydrate utilization testing. Serological assays, including coagglutination and fluorescent antibody staining have also been described for the detection of *N. gonorrhoeae*. See, Morello et al., supra. Recently, the use of DNA probes for the diagnosis of *N. gonorrhoeae* has also been reported by Morello et al., supra. The Gram-stain and antibody-based tests are rapid (<1 hour), but of low sensitivity (requiting at least $10^4$ CFU (colony forming units) bacteria per ml). Culture methods, while sensitive to approximately 2 CFU per ml, require overnight incubation.

The use of specific polynucleotide sequences as probes for the recognition of infectious agents is becoming a valuable alternative to problematic immunological identification assays. For example, PCT publication WO84/02721, published 19 Jul. 1984 describes the use of nucleic acid probes complementary to targeted nucleic acid sequences composed of ribosomal RNA, transfer RNA, or other RNA in hybridization procedures to detect the target nucleic acid sequence. Analogously, Miyada, C. G. and Born, T. L. (1991), *Molecular and Cellular Probes* 5: 327–35, used probes to detect *N. gonorrhoeae*. While the assay may provide greater sensitivity and specificity than known DNA hybridization assays, hybridization procedures which require the use of a complementary probe are generally dependent upon the cultivation and/or enrichment of a test organism and are, therefore, unsuitable for rapid diagnosis. Probes can be used directly on clinical specimens if a means of amplifying the DNA or RNA target is available.

There is a continued need for a simple, rapid, sensitive and specific diagnostic technique for the detection of *N. gonorrhoeae* in clinical samples.

In addition, patients infected with *N. gonorrhoeae* are often also infected with *Chlamydia trachomatis*. To minimize the number of diagnostic procedures to which a patient is subjected, as well as to minimize the cost of overall diagnosis, it would be highly desirable to have a simple, rapid and sensitive diagnostic technique for the simultaneous detection and identification of *N. gonorrhoeae* and *C. trachomatis* in one test procedure. The novel probes and techniques of the present invention which render it feasible to simultaneously detect *N. gonorrhoeae* and *C. trachomatis* is an additional feature of the present invention.

Use of the polymerase chain reaction ("PCR") has revolutionized the detection of a wide variety of bacterial, fungal, viral and parasitic pathogens. Enrichment and in vitro culturing of the pathogen is not required, and a relatively crude clinical specimen can provide the source of the nucleic acid for detection and diagnosis. PCR effects the targeted amplification of a specific nucleic acid sequence which dramatically increases the number of copies for detection and concomitantly reduces the complexity of the nucleic acid being analyzed.

The published sequence of a 1044 base pair fragment (ORF 1) of *N. gonorrhoeae* DNA is set forth in Miyada and Born, supra. Probes based on this ORF 1 sequence were shown to hybridize to 105 of 106 *N. gonorrhoeae* strains tested using a chromosomal dot blot format. Cross reactivity to other Neisseria species was only observed with *N. mucosa*, however this cross reactivity was eliminated with a high stringency wash. The protein coded for by ORF 1 was identified as having significant homology to the *N. gonorrhoeae* cytosine DNA methyltransferase gene (M. Ngo PII).

SUMMARY OF THE INVENTION

The present invention pertains to methods and reagents for the rapid detection and identification of the bacterium *N. gonorrhoeae*. More specifically, the present invention relates to methods and reagents for the detection of *N. gonorrhoeae* which are compatible with the simultaneous detection of *C. trachomatis* in a single assay. The detection is based upon the hybridization of nucleotide probes to nucleotide sequences present in a defined species but not in others.

In the present invention, an assay utilizing the PCR process to detect the presence of *N. gonorrhoeae* DNA in biological specimens was developed and tested using the *N. gonorrhoeae* cytosine methyl transferase (CMT) gene sequence as a target. In addition, the reagents required for *N. gonorrhoeae* detection were combined with the reagents for the detection of *C. trachomatis* to produce a single mixture reaction that independently, simultaneously and specifically amplified and detected both organisms. The sensitivity and specifity of the assay were established once conditions for the optimization of the PCR process and for the simultaneous amplification and detection of both organisms were determined. A wide variety of *N. gonorrhoeae* isolates as well as *N. gonorrhoeae* and *C. trachomatis* combined isolates were obtained from different geographic locations and were analyzed. Furthermore, the present invention permits the simultaneous amplification and detection of both *C. trachomatis* and *N. gonorrhoeae* in the same biological specimens without the need for culture enhancement and/or microscopic evaluation of specimens. Current serological tests only measure antibody response to infection, and thus are not good indicators for monitoring therapy or disease recurrence.

In a preferred embodiment, a target region from *N. gonorrhoeae* genomic DNA is amplified by PCR under defined conditions and using defined primers. The resultant amplified DNA is detected with a defined probe. The invention thus also relates to specific probes and their complements for identifying the bacterium N. gonorrhoeae. It also pertains to unique oligonucleotide sequences, mutants, fragments and subsequences thereof, from which such specific probes were derived, and includes the anti-sense sequence for any specific sequence identified.

In addition, the unique sequences of primers to be used in PCR, as well as the conditions therefor, are described herein.

The invention further provides methods of amplification and associated reagents for kits containing bacterial primers for amplifying a specific target region of N. gonorrheae DNA and probes which hybridize to a nucleotide sequence which is characteristic of N. gonorrhoeae within that target region. In addition, the invention provides methods of co-amplification of both N. gonorrhoeae and C. trachomatis, and the associated reagents therefor, as well as kits containing primers for co-amplification of both N. gonorrhoeae and C. trachomatis DNA's, as well as probes which hybridize specifically within the amplified target regions of both species.

BRIEF DESCRIPTION OF THE DRAWINGS

FIG. 1 shows the nucleotide sequence data for primers SS01 and SS02, which were used to amplify a target region in the cytosine DNA methyl transferase (CMT) gene from N. gonorrhoeae by PCR. Probe SS06-T5 is specific for a region with the 201 base pair amplified sequence.

FIG. 2 shows the nucleotide sequence data for primers CP24 and CP27 which were used to amplify a target region in the cryptic plasmid DNA from C. trachomatis by PCR. Probe CP35 is specific for a region within the 207 base pair amplified sequence.

DETAILED DESCRIPTION OF THE INVENTION

Figure 3:
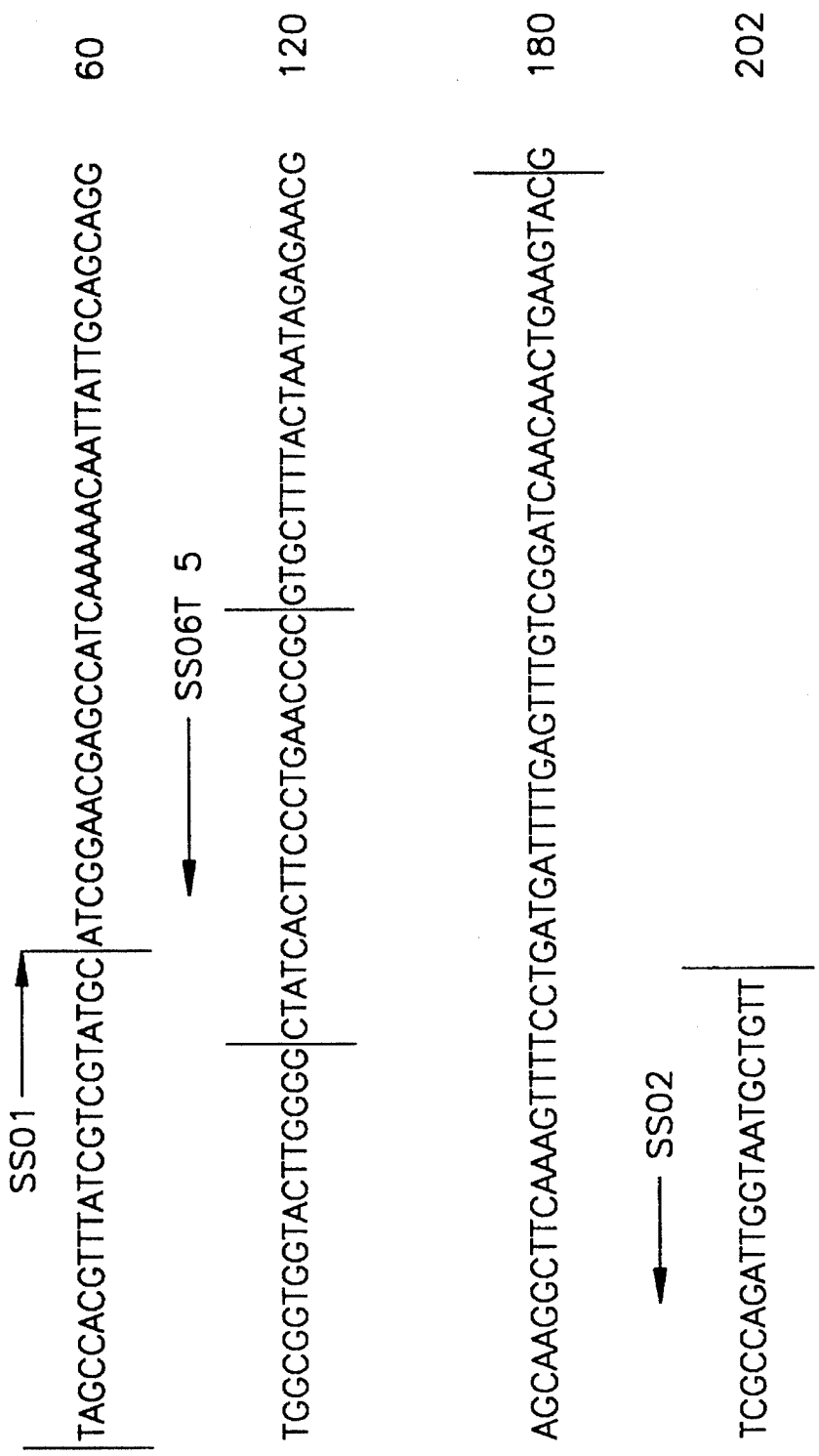
FIG. 3 shows the nucleotide sequence for the 201 base pair target region in the CMT gene from N. gonorrhoeae to which the above primers (FIG. 1) are specific.

The present invention is a method for determining the presence of and identifying the bacterium N. gonorrhoeae by means of hybridizing probes to amplified nucleotide sequences that are characteristic of that species of bacteria. The invention further provides a method for determining the presence of both N. gonorrhoeae and C. trachomatis from a single specimen by means of co-amplification.

Definitions

The following terms, as used in this disclosure and claims, are defined as:

co-amplification: the process of primer initiated synthesis from more than one target region. Multiple primer sets are combined in conditions favorable for the synthesis of primer extension products from all potential target sequences (sometimes referred to as a "multiplex" system).

complementary: means that the base sequences of a pair of a single stranded DNA or RNA molecules permit those single strands to form a hybrid or double stranded DNA:DNA, RNA:RNA or DNA:RNA through hydrogen bonding between Watson-Crick base pairs on the respective strands. Adenine (A) usually complements thymine (T) or uracil (U), while guanine (G) usually complements cytosine (C).

hybrid: the complex formed between two single stranded nucleic acid sequences by Watson-Crick base pairings or non-canonical base parings between the complementary bases.

hybridization: the process by which two complementary strands of nucleic acids combine to form double stranded molecules (hybrids).

nucleic acid probe (or just probe): a single stranded nucleic acid sequence that will combine with a complementary single stranded target nucleic acid sequence to form a double-stranded molecule (hybrid). A nucleic acid probe may be an oligonucleotide or a nucleotide polymer.

nucleotide: a subunit of a nucleic acid consisting of a phosphate group, a 5' carbon sugar and a nitrogen containing base. In RNA, the 5' carbon sugar is ribose. In DNA, it is a 2-deoxyribose. The term also includes analogs of such subunits.

oligonucleotide: a nucleotide polymer generally about 10 to about 100 nucleotide in length, but which may be greater than 100 nucleotides in length.

primer: a single stranded nucleic acid sequence, whether occurring naturally as in a purified restriction digest or produced synthetically, which is capable of acting as a point of initiation of synthesis when placed under conditions in which synthesis of a primer extension product which is complementary to a nucleic acid strand is produced, i.e., in the presence of nucleotides and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer may have modifications to the 5'-end of the molecule, such as biotinylation.

stringency: relates to the conditions used to promote hybridization of single-stranded nucleic acids (and also the conditions used to wash the hybrids formed). The degree of stringency determines how complementary the sequences of two single-stranded nucleic acids need to be in order to form a stable hybrid. When highly stringent conditions are used, only closely related nucleic acids (i.e., single-stranded nucleic acids whose sequences are almost perfectly complementary) form stable hybrids. Less stringent hybridization conditions permit the formation of hybrids between more distantly related nucleic acids (i.e., single-stranded nucleic acids whose sequences are only partially complementary).

In accordance with this invention, we have determined the target region of N. gonorrhoeae through a comparative analysis of the DNA sequences of various different strains of N. gonorrhoeae, published in the literature. As a result of our analysis, we have determined the target sequences as a region of 201 base pairs within the 1044 base pair ORF 1 fragment described in Miyada and Born, supa. The target sequence is illustrated in FIG. 3.

Further in accordance with the present invention, we designed oligonucleotide primers sufficiently complementary to a portion of the target sequence (see FIG. 3) and its complement thereof, so as to be able to hybridize to a portion of this target sequence. In accordance with this invention, the primers are designed either for the target sequences or for their complementary sequences. In this manner, these primers are sufficiently complementary to separate strands of N. gonorrhoeae DNA, so as to hybridize to one of said strands. Each of said primer is designed so as to hybridize to a separate DNA strand. In this manner, through the identification of the target nucleotide sequence of various strains of *N. gonorrhoeae* DNA, one can utilize these primers in the polymerase chain reaction (PCR) to amplify the target nucleic acid sequence of *N. gonorrhoeae* DNA in samples suspected of containing *N. gonorrhoeae*. In accordance with this invention, we have found that oligonucleotide primers containing at least 10 nucleotides can be utilized in carrying out this reaction. Generally, the nucleotide primers contain from about 10 to 30 nucleotides.

In accordance with this invention, the primer is sufficiently complementary to hybridize to a separated strand of the DNA of *N. gonorrhoeae* to hybridize thereto and, when amplified by means of said polymerase chain reaction, will form an extension product containing the target DNA sequence. The target DNA sequence can be detected by hybridization to suitable oligonucleotide probes containing at least 14 nucleotides and which are substantially complementary to a polynucleotide sequence of said target region. Generally, these oligonucleotide probes contain from about 14 to about 30 nucleotides.

In accordance with the present invention, oligonucleotides containing sequence SS01 (SEQ ID NO: 1), SS02 (SEQ ID NO: 2), and SS06-T5 (SEQ ID NO: 3), as set forth in FIG. 1 were prepared. These oligonucleotides were utilized to design the primers and probes in accordance with this invention.

An important feature of this invention is that the oligonucleotides which function as the primers for the invention not only select specifically for *N. gonorrhoeae*, but in addition, have physical properties such as melting temperatures, etc., which are compatible with the primers used in a PCR-based *C. trachomatis* assay. Thus, applicants' *N. gonorrhoeae* oligonucleotides are specific for *N. gonorrhoeae*, do not interact or otherwise cross-react with *C. trachomatis*, and are compatible with the *C. trachomatis* primer oligonucleotides such as to enable simultaneous amplification of *N. gonorrhoeae* and *C. trachomatis* in a single, PCR reaction.

In accordance with this invention, the test for the presence of *N. gonorrhoeae* in samples is carried out by treating samples with an aqueous solution containing the oligonucleotide primers which are sufficiently complementary to the separate strands of *N. gonorrhoeae* DNA to hybridize thereto. The solution which is utilized to treat the sample could contain as a cosolvent an inert organic polar solvent. Any conventional inert organic polar solvent can be utilized as a component of the aqueous solution. In accordance with the preferred embodiment of this invention, the polar solvent which is used as a cosolvent can be glycerol, dimethylsulfoxide or fomamide, or mixtures thereof. Furthermore, in accordance with the preferred embodiment of this invention, the cosolvent should constitute from about 1% to about 20% by volume of the solution which is utilized to treat the sample to be tested.

The unique sequences of the primers used in the invention are described herein below, as well as the preferred or essential PCR conditions.

The polymerase chain reaction (PCR) is a powerful technique that can be used for the detection of small numbers of pathogens whose in vitro cultivation is difficult or lengthy, or as a substitute for other methods which require the presence of living specimens for detection. In its simplest form, PCR is an in vitro method for the enzymatic synthesis of specific DNA sequences, using two oligonucleotide primers that hybridize to opposite strands and flank the region of interest in the target DNA. A repetitive series of cycles involving template denaturation, primer annealing, and the extension of the annealed primers by DNA polymerase results in the exponential accumulation of a specific fragment whose termini are defined by the 5' ends of the primers. PCR reportedly is capable of producing a selective enrichment of a specific DNA sequence by a factor of $10^{12}$. The PCR method is described in Saiki et al., Science 230:1350 (1985) and is the subject, inter alia. of U.S. Pat. Nos. 4,683,195, 4,683,202, 4,800,159 and 4,965,188. This method has been used to detect the presence of the aberrant sequence in the beta-globin gene, which is related to sickle cell anemia (Saiki et al., (1985) supra) and human immunodeficiency virus (HIV) RNA (Byrne et al., Nuc Acids Res 16:4165 (1988)).

The invention provides methods for determining the presence of the *N. gonorrhoeae* DNA in a fluid sample suspected of containing *N. gonorrhoeae*, if *N. gonorrhoeae* is present, comprising:

(a) treating said sample with an aqueous solution containing at least two oligonucleotide primers sufficiently complementary to the separate strands of said DNA to hybridize thereto, said solution containing as a cosolvent an inert organic polar solvent;

(b) synthesizing an extension product of each of said primers, which extension products contain the target DNA sequence, and amplifying said target sequence, if any is present, to a detectable level;

(c) treating said sample, after the intended amplification, with an oligonucleotide probe containing at least fourteen nucleotides which are substantially complementary to a sequence in the amplified target region;

(d) incubating the amplified target region, if any, with the oligonucleotide probe under conditions which allow for hybridization between the probe and said target region (specificity of hybrid duplexes); and (e) detecting hybrids formed between the amplified target region, if any, and the oligonucleotide probe.

Preferred organic polar solvents include glycerol, dimethyl sulfoxide or formamide, most preferably glycerol. Said cosolvent is typically present in said solution in about 1% to 20% by volume.

Preferably, when used as a diagnostic method, in step (d) above, the probe hybridizes specifically to the target region under high stringency conditions. In addition, the primers specific for *N. gonorrhoeae* are also uniquely selective for the amplification of *N. gonorrhoeae* under selected amplification conditions.

The invention also provides methods for determining the presence of either or both *N. gonorrhoeae* DNA and *C. trachomatis* DNA in a fluid sample suspected of containing *N. gonorrhoeae* and/or *C. trachomatis*, comprising:

(a) treating said sample with an aqueous solution containing 2 sets of oligonucleotide primers (one set specific for *N. gonorrhoeae* and one set specific for *C. trachomatis*) sufficiently complementary to separate strands of said DNA to hybridize thereto;

(b) synthesizing an extension product of each of said primers, which extension products contain the target DNA sequence, and amplifying said target sequence, if any is present, to a detectable level;

(c) treating said sample, after the intended amplification, with 2 oligonucleotide probes, each of which contains at least fourteen nucleotides: one probe containing a sequence uniquely complementary to a sequence in the amplified region of *N. gonorrhoeae*; and a second probe containing a sequence uniquely complementary to a sequence in the amplified region of *C. trachomatis;*

(d) incubating the amplified target region(s), if any, with each of the oligonucleotide probes, preferably in separate vessels, under conditions which allow for hybridization between each of said probes and the target region for said probe; and (e) detecting hybrids formed between the amplified target regions, if any, and the oligonucleotide probes.

Preferably, when used as a diagnostic assay, step (d) above is carried out under high stringency conditions to eliminate formation of hybrids between the probe and those target sequences that are only partially complementary.

The methods of the present invention thus enable determination of the presence of the suspected target organisms more rapidly than heretofore possible with prior art detection methods. The basic PCR process is carried out as described below.

A sample is provided which is suspected of containing a particular nucleic acid sequence of interest, the "target sequence". The nucleic acid contained in the sample may be denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 150° C., for times ranging from about 5 seconds to 10 minutes using current technology.

The denatured DNA strands are then incubated with the selected oligonucleotide primers under hybridization conditions, conditions which enable the binding of the primers to the single nucleic acid strands. As is known in the art, the primers are selected so that their relative positions along a duplex sequence are such that an extension product synthesized from one primer, when it is separated from its complement, serves as a template for the extension of the other primer to yield a replicate chain of defined length.

The primer must be sufficiently long to prime the synthesis of extension products in the presence of the agent for polymerization. The exact length of the primers will depend on many factors, including temperature, source of the primer and use of the method. For example, depending on the complexity of the target sequence, the oligonucleotide primer typically contains about 15–30 nucleotides, although it may contain more or fewer nucleotides. Short primer molecules generally require cooler temperatures to form sufficiently stable hybrid complexes with the template. The primers must be sufficiently complementary to hybridize selectively with their respective strands.

The primers used herein are selected to be "substantially" complementary to the different strands of each specific sequence to be amplified. This means that the primers need not reflect the exact sequence of the template, but must be sufficiently complementary to hybridize selectively with their respective strands, that is to strands of *N. gonorrhoeae* DNA and not to strands of other DNA from other Neisseria species, under given amplification conditions. This property is referred to as the "specificity" of the primers. Non-complementary bases or longer sequences can be interspersed into the primer, provided that the primer is sufficiently complementary to the sequence of one of the strands to hybridize specifically therewith, and to thereby form a duplex structure which can be extended by the polymerizing means. The non-complementary nucleotide sequences of the primers may include restriction enzyme sites. Appending a restriction enzyme site to the end(s) of the target sequence is particularly helpful for subsequent cloning of the target sequence.

The primers of the present invention are unique in that they are not only "substantially" complementary to a portion of a target sequence that is specific for *N. gonorrhoeae* and not other Neisseria species, but in addition, have physical characteristics that enable them to be compatible with (i.e., do not interfere with and are not interfered by) a different set of primers used for the simultaneous amplification and/or detection of *C. trachomatis* in a single assay (i.e., single tube amplification of two different species). The primers chosen for this co-amplification are uniquely specific for each species, have similar melting temperatures, are not complementary to each other and result in amplified products of similar sizes.

The oligonucleotide primers and probes of the present invention may be prepared by any suitable method. Methods for preparing oligonucleotides of specific sequence are known in the art, and include, for example, cloning and restriction digestion of appropriate sequences, and direct chemical synthesis. For ease of detection, the primers or probes may be labeled, if desired, by incorporating compounds detectable by spectroscopic, photochemical, biochemical, immunochemical, or chemical means.

Template-dependent extension of the oligonucleotide primer(s) is then catalyzed by a polymerizing agent in the presence of adequate amounts of the four deoxyribonucleoside triphosphates (dATP, dGTP, dCTP, and dTTP) or analogs, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, $T_4$ DNA polymerase, Taq DNA polymerase, Tth DNA polymerase from *Thermus thermophilus* and DNA polymerase from *Thermococcus litoralis*. The reaction conditions for catalyzing DNA synthesis with these DNA polymerases are well known in the art.

The products of the synthesis are duplex molecules consisting of the template strands and the primer extension strands, which include the target sequence. These products, in turn, serve as templates for another round of replication. In the second round of replication, the primer extension strand of the first cycle is annealed with its complementary primer; synthesis yields a "short" product which is bounded on both the 5'- and the 3'-ends by primer sequences of their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method can be performed in a number of temporal sequences. For example, it can be performed step-wise, where after each step new reagents are added, or in a fashion where all of the reagents are added simultaneously, or in a partial step-wise fashion, where fresh reagents are added after a given number of steps.

In a preferred method, the PCR reaction is carried out as an automated process which utilizes a thermostable enzyme. In this process the reaction mixture is cycled through a denaturing step, a primer annealing step, and a synthesis step. A DNA thermal cycler specifically adapted for use with a thermostable enzyme may be employed, which utilizes temperature cycling without a liquid-handling system, thereby eliminating the need to add the enzyme at every cycle. This type of machine is commercially available e.g., from the Perkin-Elmer Corporation.

After amplification by PCR, the target polynucleotides may be detected directly by gel analysis provided the target DNA is efficiently amplified and the primers are highly specific to the target region to be amplified. To assure PCR efficiency, glycerol and other related solvents such as dimethyl sulfoxide, can be used to increase the sensitivity of the PCR at the amplification level and to overcome problems pertaining to regions of DNA having strong secondary structure. These problems may include (1) low efficiency of the PCR, due to a high frequency of templates that are not fully extended by the polymerizing agent or (2) incomplete denaturation of the duplex DNA at high temperature, due to high GC content. The use of such solvents can increase the sensitivity of the assay at the level of amplification to approximately several femtograms of DNA (which is believed to correspond to a single bacterial cell).

Alternatively, the target polynucleotides may be detected by hybridization with a polynucleotide probe which forms a stable hybrid with that of the target sequence under stringent to low stringency hybridization and wash conditions. If it is expected that the probes will be completely complementary (i.e., about 99% or greater) to the target sequence, stringent conditions will be used. If some mismatching is expected, for example if variant strains are expected with the result that the probe will not be completely complementary, the stringency of hybridization may be lessened. However, in the context of a diagnostic application, sufficiently stringent conditions are chosen to rule out hybridization of the probe to targets that are only partially complementary (e.g., a related DNA sequence from a different species).

Conditions which affect hybridization and which select against hybridization with partially complementary sequences are known in the art. For example, it is known that stringency is a function of temperature, salt concentration, length of probe, GC content of the probe and concentration of chaotropic agents in the hybridization buffers. For a given probe, starting from a particular set of conditions, decreasing the salt concentration, increasing the temperature or increasing the chaotrope concentration results in an increase in stringency.

In a preferred embodiment of the present invention, the target polynucleotides are incubated with an oligonucleotide probe in the presence of a buffer having a concentration of from about 2.5M to about 4.5M, preferably from about 3.8M to about 4.2M, most preferably 4.0M, sodium isothiocyanate, at a temperature of from about 35° C. to about 40° C., preferably from about 37° C. to about 39° C., thereby allowing for high stringency during hybridization.

Probes for target sequences may be derived from either strand of the amplified duplex. The probes may consist of the bases A, G, C or T or analogs (including inosine and 5-methyl-cytosine). The probes may be of any suitable length which span a portion of the target region, but which exclude the primers, and which allow specific hybridization to the target region. Generally, the probes will have at least 14 nucleotides, preferably at least 18 nucleotides, and more preferably at least 20 to 30 nucleotides of either of the complementary DNA strands. If there is to be complete complementarity, i.e., if the strain contains a sequence identical to that of the probe, the duplex will be relatively stable under even stringent conditions and the probes may be short, i.e., in the range of about 10–30 basepairs. If some degree of mismatch is expected with the probe, i.e., if it is suspected that the probe will hybridize to a variant region, the probe may be of greater length, since length seems to counterbalance some of the effect of the mismatch(es). The probe may be formed from a subset of the target region and therefore need not span the entire target region. Any subset of the target region has the potential to specifically identify the target region.

If desired, the probe may also be labeled. A variety of labels which would be appropriate, as well as methods for their inclusion in the probe are known in the art, and include, for example, radioactive atoms, such as $^{32}P$, or other recognizable functionalities e.g., biotin (preferably using a spacer arm), fluorescent dyes, electron-dense reagents, enzymes capable of forming easily detectable reaction products (e.g., alkaline phosphatase, and horseradish peroxidase), or antigens for which specific antisera or monoclonal antibodies are available.

The probe may also be covalently attached to a protein, such as BSA, to attach the probe to a surface, such as a plastic microwell plate, a nylon membrane, or magnetic microsphores.

In order to obtain probes to be used for the PCR assays described herein, enough of the nucleotide sequence of the target region must be known. Analysis of the nucleotide sequence of the target region may be direct analysis of the PCR amplified products as described in Gyllensten and Erlich, Proc. Natl. Acad. Sci. USA 85:7652 (1988) and in U.S. Ser. No. 248,896, filed Sep. 23, 1988 which issued as U.S. Pat. No. 5,066,584. A modification of this procedure involves separating the duplex DNA strands of the target region and generating a single stranded DNA template for use in the sequencing reactions (Mitchell and Merrill, ref). Alternatively, the isolated PCR amplified DNA fragments may be cloned into vectors and the resulting DNA obtained from bacteria transformed with insert-containing vector DNA is then sequenced.

In the present invention, PCR is used to detect the bacterium *N. gonorrhoeae* by in vitro amplification of part of the putative CMT gene. The system has a high analytical sensitivity; the detection limit using purified nucleic acid is one organism's equivalent of DNA. Hybridization with an oligonucleotide probe provides the assay with an additional level of specificy for *N. gonorrhoeae*.

In a preferred embodient, a diagnostic assay for *N. gonorrhoeae* comprises:

1) amplification of a treated clinical specimen with biotin-labeled primers specific for the putative CMT gene of *N. gonorrhoeae*. The preferred primers, SS01 and SS02, correspond to a highly conserved region in the CMT gene. The resulting amplified product is 201 base pairs, corresponding to base pairs 773–974 of the 1044 base pair gene (See Miyada and Born, supra); and 2) subjecting the amplified sample to a stringent hybridization with an oligonucleotide probe bound to a solid support. The preferred probe, a 20 base pair probe (SS06-T5), is specific for a region within the 201 base pair target sequence and was selected to eliminate cross reactivity with *N. mucosa* that was observed using each of the probe sequences tested by Miyada and Born, supra.

In another preferred embodiment of the present invention, a single PCR assay is run which utilizes 2 primers specific for *N. gonorrhoeae* and two additional primers specific for *C. trachomatis*. These two sets of primers are selected so as not to interfere (cross-react) with each other. Following amplification, the target sample is separately hybridized to two different probes bound to two different solid supports. One probe is specific for the amplified target sequence of *N.* gonorrhoeae and the other probe is specific for the amplified target sequence of *C. trachomatis.*

The amplification efficiency, and thus overall sensitivity, of the above described *N. gonorrheae/C. trachomitis* PCR assay is critically dependent on the compatibility of the 2 primer sets. The primers designed for the present invention, along with being uniquely specific for each species as discussed above, meet 4 additional major criteria (see FIGS. 1 & 2): (1) the primers are of similar length and GC content and therefore have similar melting temperatures; 2) amplifications directed by the primers have a similar $MgCl_2$ optimum; 3) there is no complementarity between the primers; and 4) the primers result in amplification products of similar sizes.

The presence of the target sequence in a biological sample is detected by determining whether a hybrid has been formed between the probe and the nucleic acid subjected to the PCR amplification techniques. Methods to detect hybrids formed between a probe and a nucleic acid sequence are known in the art. For example, an unlabeled sample may be transferred to a solid matrix to which it binds, and the bound sample subjected to conditions which allow specific hybridization with a labeled probe; the solid matrix is then examined for the presence of the labeled probe. Alternatively, if the sample is labeled, an unlabeled probe is bound to the matrix, and after exposure to the appropriate hybridization conditions, the matrix is examined for the presence of a label. Saiki et al., Proc Natl Acad Sci, USA 86:6230–6234 (1989) describe methods of immobilizing multiple probes on a solid support and using hybridization to detect the amplified target polynucleotides of interest. See also U.S. application Ser. No. 07/414,542 Longiaru et al which issued as U.S. Pat. No. 5,232,829. The latter two procedures are well suited to the use of a panel of probes which can provide simultaneous identification of more than one pathogen in a single clinical sample. In another alternative procedure, a solution phase sandwich assay may be used with labeled polynucleotide probes, and the methods for the preparation of such probes are described in U.S. Pat. No. 4,820,630, issued 11 Apr. 1989.

The probes described herein are preferably applied to the detection of *N. gonorrhoeae* and *C. trachomatis.* All of the probes described below, as well as any additional probes, can be fixed to the surface of a microwell plate as is described for example in copending and co-owned U.S. Ser. No. 08/141,355. Each of the probes is immobilized on a separate well of a microtiter plate. The labelled, amplified DNA is hybridized to each of the probes in an aqueous solution. The pattern of the signals from each well (i.e., probes) indicates the identity of the target DNA. Thus, upon amplification of the target region (e.g., by PCR), and application of the probes described herein, hybridization to one or both of the probes will result in a positive signal and the positive identification of *N. gonorrhoeae* and/or *C. trachomatis.*

Also within the scope of the present invention are PCR kits for use in carrying out any of the aforementioned PCR amplification and/or detection processes. The diagnostic kits include the oligonucleotide probes and the primers decribed in this application. The primers and probes may be labeled, such as, for example, with biotin. If the primers are labeled, the probes may be fixed to a microwell plate. The kit may also contain other suitably packaged reagents and other materials needed for the particular assay protocol, for example, controls, and polymerizing agents, as well as instructions for conducting the test.

In use, the components of the PCR kit, when applied to a nucleic acid sample, create a reagent mixture which enables the detection and amplification of the target nucleic acid sequence. The reagent mixture thus includes the components of the kit as well as a nucleic acid sample which contains the polynucleotide chain of interest.

A variation of this approach is to use an alternate method of producing the amplified target region. For example, the TAS amplification system (Kwoh, et al., Transcription-based amplification system and detection of amplified human immunodeficiency virus type I with a bead-based sandwich hybridization format, Proc. Natl. Acad. Sci. USA 86:1173–1177 (1989)) and its modification, SSSR (Guatelli, et al., "Isothermal, in vitro Amplification of Nucleic Acids by a Multi-Enzyme Reaction Modeled After Retroviral Replication.," Proc. Natl. Acad. Sci. USA 87:1874–1878 (1990)) is a method for amplifying RNA or DNA using cycles consisting of a cDNA step to produce a cDNA copy of the template and an RNA transcription step to increase the copy number of the cDNA template. This method, like PCR, employs two oligonucleotide primers which hybridize to opposite strands of the target region and flank the target region. The primers described herein may, with minor modifications (the addition of RNA polymerase promoter sequences at the 5' end of one of the primers), be used in a TAS or SSSR amplification system. The subsequent step of the assay, detection by the oligonucleotide probes described herein, may be carried out essentially as described above for the PCR-based assay or may be done using a bead-based sandwich hybridization system (Kwoh, et al).

In another example, the probes described herein could be used as a component of the probes in a signal amplification system such as the Q-beta replicase system (Kramer and Lizardi, "Replicatable RNA Reporters," Nature 339:401–402 (1989), and Lomeli, et al., "Quantitive Assays Based on the Use of Replicatable Hybridization Probes," Clin. Chem. 35:1826–1831 (1989)). This system involves an RNA probe containing the specific probe sequence inserted into the MDV-1 variant of the Q-beta RNA genome. The RNA probe is replicated using Q-beta replicase, producing up to $10^{12}$ molecules per reaction, after hybridization of the probe to the sample to be assayed.

By way of further specificity, the following probe and primer nucleotide sequence data is provided:

Primer SS01 (SEQ ID NO: 1) (FIG. 1) corresponds to nucleotide base numbers 773–796 of the *N. gonorrhoeae* M•NgO P11, cytosine DNA methyltransferase gene, as specified in Miyada and Born, supra.

Primer SS02 (SEQ ID NO: 2) (FIG. 1) corresponds to the complement of the nucleotide base numbers 952–974 in the *N. gonorrhoeae* M•NgO P11, cytosine DNA methyltransferase gene, as specified in Miyada and Born, supra.

Probe SS06-T5 (SEQ ID NO: 3) (FIG. 1) corresponds to the complement of nucleotide base numbers 851–870 in the *N. gonorrhoeae* M•NgO P11, cytosine DNA methyltransferase gene, as specified in Miyada and Born, supra (corresponding to base numbers 79–98 in applicants' FIG. 3).

EXAMPLE 1

Evaluation of assay performance and sensitivity

The co-amplification assay designed for the detection of *N. gonnorrhoeae* and *C. trachomatis* employs 2 primer sets: 1) SS01, SS02 for *N. gonorrhoeae*; and 2) CP24, CP27 for *C. trachomatis.* All 4 primers are labeled with Biotin at their 5' ends, to facilitate the detection of amplified products following PCR. To determine the performance and sensitivity of the assay, the following experiment was performed.

A, PCR amplification of purified DNA

Purified extracts of *N. gonorrhoeae* chromosomal DNA and *C. trachomatis* plasmid DNA were serially diluted in a solution of 0.2% SDS, 10% TWEEN 20 (polyoxyethlene-sorbitan monolaurate), 10 mM Tris (pH 8.5), 3 mM $MgCl_2$, and 0.05% $NaN_3$ (STM+Specimen Diluent, see Example 3). The DNA samples were diluted to deliver X copies (any desired number) in 50 ul of diluent. Aliquots ranging from as little as 2 copies/50 ul up to 100 copies/50 ul were mixed with 50 ul of 2× PCR mix. The final concentration of the reaction components was as follows:

10 mM Tris pH 8.5

50 mM KCL 1.5 mM $MgCl_2$ 50 uM EDTA

10% Glycerol 0.05% $NaN_3$ 50 uM dGTP, 50 uM dCTP, 50 uM dATP, 150 uM dUTP 0.25 uM Bio SS01, 0.25 uM Bio SS02

0.25 uM bio CP24, 0.25 uM Bio CP27

5 units per reaction Taq polymerase 2 units per reaction Amperase

Each 100 ul reaction was aliquotted into a PCR Micro-Amp tube, loaded in a sample tray and placed in a thermal cycler (TC-9600 Perkin-Elmer, Norwalk, Conn.).

The following amplification parameters were used:

| Cycle 1: | 2 min., 50° C. | 1 cycle |
| --- | --- | --- |
| Cycle 2: | 5 min., 95° C. | 1 cycle |
| Cycles 3–37: | 20 sec., 95° C. | 35 cycles |
| | 20 sec., 62° C. | |
| | 20 sec., 72° C. | |
| Cycle 38 | Hold at 72° C. for 10 minutes (can be stopped at user's discretion) | 1 cycle |

B. Detection of amplified products

As the primers for both targets were biotinylated, it was therefore possible to perform a capture hybridization assay for the colorimetric detection of labeled amplified products.

Capture probe CP35, specific for *C. trachomatis* was fixed to the bottom of the wells of a microtiter plate via a thioether linkage to bovine serm albumin (Barone, et al., Microtiter plate detection of *Chlamydia trachomatis* employing PCR. Abstracts for the general meeting of the American Society of Microbiology, 1991, p. 361). The capture probe for *N. gonorrhoeae*, SS06-T5, was fixed in the same fashion to the wells of another plate.

Following co-amplification, each reaction was denatured with 100 ul of 0.4N NaOH, 80 mM EDTA. One 25 ul aliquot was added to a well on the CP35 plate. A second 25 ul aliquot was added to a well on the SS06-T5 plate. Each well contained 100 ul of a hybridization/neutralization solution consisting of 2.5M NaSCN, 80 mM $NaH_2PO_4$, 10 mM $Na_2HPO_4$ and 0.125%.

The plates were incubated for 1 hour at 37° C. The wells were then washed 5 times with 350 ul of 150 mM NaCl, 7 mM $Na_2HPO_4$, 3 mM $NaH_2PO_4$, 0.125% TWEEN 20 (polyoxyethylenesorbitan monolaurte), 0.05% Proclin 300 and 1 mM EDTA pH 7.5.

100 ul of Avidin-HRP conjugate was added to each well and incubated for 15 minutes at 37° C. The wells were washed 5 times in the same manner as described above. 100 ul of a 3,3',5,5'-tetramethylbenzidine ("TMB") and hydrogen peroxide substrate was added to each well and the color reaction was allowed to develop for 10 minutes in the dark. The reaction was stopped with 100 ul per well of a $H_2SO_4$ stop reagent. Plates were read at 450 nm in a microwell plate reader. Readings greater than 0.25 were called positive.

The date generated, from the amplification of this purified DNA titration yielded signals well above the linear range (0–3.0 OD units) of the microwell plate reader, and as such are not shown. Following 38 cycles of amplification, as little as 2 input copies of "clean target" DNA generated more amplified product than could be linearly evaluated by the plate capture hybridization assay. These results indicated a very high level of performance and sensitivity for the assay.

EXAMPLE 2

Determination of *Neisseria gonorrhoeae* primer and probe specificity

A. PCR Amplification

PCR amplification was performed on 15 strains of *N. gonorrhoeae*, 32 strains of other Neisseria species and 13 other relevant organisms. The specific organisms and strains are summarized below in Table 1. 50 ul of each DNA extract (in STM+specimen diluent, see Example 3) were mixed together with 50 ul of 2× PCR mix and amplified as described in Example 1.

B. Detection of amplified products

After the amplification reactions were complete, 5 ul of each 100 ul reaction, were loaded onto a 2% Nusieve agarose gel in 1× TBE (45 mM Tris-Borate, 1 mM EDTA) and 5 ug/ml ethidium bromide. After running, the gel was photographed under UV light. The results, expressed as the presence (+) or absence (−) of a band of the appropriate size (201 bp), are shown in Table 1.

C. Transfer of amplified DNA's to nylon membrane

After photography of the gel, the gel was soaked in 0.25N HCl for 10 minutes at room temperature. The gel was then soaked in a solution of 0.5N NaOH, 1.5M NaCl for 30 minutes, followed by soaking in a solution of 1M Tris (pH 7.5), 1.5M NaCl for 30 minutes.

The DNA was transferred to a nylon membrane by electroblotting for 1 hour at 40° C. in 1×TBE. The filter was subsequently rinsed in 1× TBE, air dried and the DNA was crosslinked using UV light in a Stratagene Stratalinker.

D. Radioactive labeling of oligo probe SS06-T5

Probe SS06-T5 (20-mer) was labeled using T4 polynucleotide kinase as follows:

| | |
| --- | --- |
| $^{32}P\text{-}\gamma\text{-ATP}$ | 6.0 ul |
| 10X Kinase Buffer | 2.5 ul |
| 10 pmoles SS06-T5 | 1.0 ul |
| T4 polynucleotide kinase | 1.0 ul |
| $dH_2O$ | 14.5 ul |
| Total | 25.0 ul |

10× Kinase Buffer:

500 mM Tris pH 8.0

100 mM $MgCl_2$ 50 mM DTT

The kinase reaction was incubated for 30 minutes at 37° C. 4.0 ul of 0.5M EDTA and 70 ul of $dH_2O$ were added to stop the reaction. The reaction mixture was loaded onto a 1.0 ml Biogel P4 column 2 times at 1200 rpm, to separate the labeled oligonucleotide from the unincorporated radioactive label. 1 ul of the eluate was counted in a scintillation counter to determine the level of radioactive incorporation. 200,00 cpm was used for each blot in the subsequent hybridization.

E. Hybridization of SS06-T5 with transferred DNA's

Six (6) DNA blots were pre-hybridized in a mixture of 5× SSPE, 0.5% SDS at 55° C. for 30 minutes (1× SSPE=0.18M NaCl, 10 mM NaPO$_4$, pH 7.4, 1 mM EDTA). The labeled oligonucleotide probe was added to 10 ml (per blot) of 5× SSPE, 0.5% SDS. The solution was added to the plastic bag containing the presoaked blot. Hybridization occurred for 1 hour at 55° C.

The blot was removed from the plastic bag and rinsed once in a solution of 5× SSPE, 0.5% SDS. The blot was then washed for 10 minutes in a solution of 2× SSPE, 0.1% SDS.

The blots were wrapped in Saran wrap and placed in an x-ray film holder with a sheet of Kodak XAR-5 x-ray film with an intensifying screen and exposed for 16 hours at −70° C.

The results of hybridization reactions are interpreted in Table 1 below. As can be seen from Table 1, a total of 10 strains from 5 different species of the non-gonorrhoeae Neisseria tested showed postive amplification with the *N. gonorrhoeae* primers (e.g. ATCC 14685 and ATCC 25296). These products, however, displayed no hybridization with the *N. gonorrhoeae* specific probe SS06-T5. The probe, therefore, provides the necessary specificity to this system which it otherwise would not have using PCR alone.

EXAMPLE 3

Clinical Specimen Evaluation

Using a preferred embodiment of the invention, 960 clinical specimens were tested using co-amplification for *N. gonorrhoeae* and *C. trachomatis*.

A. Specimen collection

1) Endocervical swabs

Endocervical swabs were placed in 1.0 ml of specimen transport medium (STM) (which comprises 0.4% SDS, 10 mM Tris, pH 8.0) for transport to a lab for analysis.

2) Urine 8.0 ml of male urine was collected and spun at 3000 rpm. The pellet was resuspended in 2.0 ml of 0.4% SDS, 190 mM Tris, pH 8.5.

B. Co-amplification of specimens

Prior to amplification, all specimens received an equal volume (1.0 ml for endocervical swabs, 2.0 ml for urine pellets) of Specimen Diluent (20% TWEEN 20 (polyyoxyethylenesorbitan monolaurate), 6 mM MgCl$_2$, 0.05% NAN$_3$, 10 mM Tris, pH 8.5). 50 ul of each specimen was added to 50 ul of 2× PCR mix. Reaction conditions and cycling parameters were as described in Example 1A.

C Detection of amplified products

The amplified products were detected as described in Example 1B. The results are shown in Table 2 for the endocervical specimens and in Table 3 for the urine specimens.

For both the endocervical and urine specimens, the high number of culture (−), PCR (+) samples for *N. gonorrhoeae* and *C. trachomatis* was not surprising due to the increased sensitivity of detection by PCR versus by standard culture methods.

EXAMPLE 4

Optimizing Hybridization Buffer Formulations for Maximal Specificity

The system described in Examples 1 and 2 when implemented into a diagnostic assay had an accuracy rate of about 99%. Occasionally, when co-amplification was performed in the presence of *C. trachomatis* and *N. gonorrhoeae* specific primer oligonucleotides, but in the absence of added sample DNA, we obtained nonspecific signals for *N. gonorrhoeae* (but not for *C. trachomatis*). These rare nonspecific signals ($A_{450}$>0.25) were observed in the presence and absence of AmpErase and, therefore, were not caused by contamination with previously amplified, dUTP-containing DNA. We investigated whether these nonspecific signals could be eliminated by increasing the stringency of the hybridization buffer. Stringency was increased by increasing the concentration of the chaotrope NaSCN in the buffer.

To determine whether increasing the stringency of hybridization buffer could reduce and/or eliminate the nonspecific *N. gonorroeae* signals, five independent co-amplification runs (each consisting of several hundred amplification reactions) were performed. The products of each amplification reaction were assayed by hybridization to an immobilized *N. gonorrhoeae*-specific probe using low (2.5M NaSCN) and high (4.0 NaSCN) hybridization buffers. After hybridization, the bound products were detected using an avidin-horseradish peroxidase conjugate (which binds to biotin residues that were incorporated into the amplified products). These data are summarized in Table 4. The frequency of nonspecific signals was reduced when products were assayed using the high stringency hybridization buffer. Furthermore, the signals of the remaining nonspecific readings were greatly reduced; many signals that were >1.0$A_{450}$ using the less stringent buffer reduced to <0.6$A_{450}$ using the more stringent buffer (results marked with an * in Table 4). A subset of nonspecific readings generated strong signals using both buffers (results marked with an ** in Table 4). These nonspecific readings appear to have been produced by contamination with genuine *N. gonorrhoeae* DNA from the environment. Unlike the other positive signals, they hybridize to a second *N. gonorrhoeae*-specific probe (SS08). This second probe and the original (SS06T5) probe are complementary to non-overlapping sequences contained within the segment of DNA amplified by the *N. gonorrhoeae*-specific primers. Thus, the positive results whose signal is reduced by increasing hybridization stringency share a limited sequence with true *N. gonorrhoeae* DNA (i.e., partially complementary to the SS06T5 probe). In contrast, the nonspecific signals that are not affected by increasing stringency contain two different *N. gonorrhoeae*-specific sequences (i.e., one sequence is complementary to SS06T5 and one sequence is complementary to SS08), as would be expected if contamination with *N. gonorrhoeae* DNA occurred.

TABLE 1

Specificity analysis of *N. gonorrhoeae* primers and probe in the PCR co-amplification assay

| Organism | | Gel Photo | Blot Hyb. SS06-T5 |
| --- | --- | --- | --- |
| *Neisseria gonorrhoeae* | 25-20 | + | + |
| | CMCC 2779 | + | + |
| | CMCC 2783 | + | + |
| | CMCC 2852 | + | + |
| | CMCC 2860 | + | + |
| | A 10 | + | + |
| | AL03418 | + | + |
| | K3 | + | + |
| | IL4 | + | + |
| | IL22 | + | + |
| | IL36 | + | + |
| | R56 | + | + |
| | R180 | + | + |

TABLE 1-continued

Specificity analysis of *N. gonorrhoeae* primers and probe in the PCR co-amplification assay

| Organism | | Gel Photo | Blot Hyb. SS06-T5 |
|---|---|---|---|
| | SF3B | + | + |
| | TX7 | + | + |
| *Neisseria cinerea* | ATCC 14685 | + | – |
| | CMCC 2791 | – | – |
| *Neisseria elongata* | ATCC 25296 | + | – |
| | STA1 | + | – |
| *Neisseria flavescens* | CMCC 2790 | – | – |
| *Neisseria lactamica* | ATCC 23970 | – | – |
| | CMCC 2792 | – | – |
| | STA32 | – | – |
| | STA177 | – | – |
| *Neisseria meningitidis* | CMCC 2801 | – | – |
| | STA5 | – | – |
| | A | – | – |
| | B | – | – |
| | C | – | – |
| | W135 | – | – |
| | Y | – | – |
| *Neisseria mucosa* | ATCC 19693 | + | – |
| | ATCC 19694 | – | – |
| | ATCC 19697 | – | – |
| | ATCC 25996 | – | – |
| | ATCC 25997 | – | – |
| | CMCC 2794 | – | – |
| | STA37 | + | – |
| | STA45 | + | – |
| | STA47 | + | – |
| *Neisseria perflava* | CMCC 2796 | – | – |
| *Neisseria sicca* | ATCC 9913 | – | – |
| | ATCC 29256 | + | – |
| | ATCC 29259 | + | – |
| | CMCC 2797 | – | – |
| *Neisseria subflava* | ATCC 14799 | + | – |
| | CMCC 2793 | – | – |
| *Branhamella catarrhalis* | ATCC 8176 | – | – |
| | CMCC | – | – |
| *Chlamydia trachomatis* | CMCC | – | – |
| *Enterobacter aerogenes* | CMCC | – | – |
| *Escherichia coli* | CMCC | – | – |

TABLE 1-continued

Specificity analysis of *N. gonorrhoeae* primers and probe in the PCR co-amplification assay

| Organism | | Gel Photo | Blot Hyb. SS06-T5 |
|---|---|---|---|
| *Gardnerella vaginalis* | CMCC | – | – |
| *Hemophilus influenzae* | CMCC | – | – |
| *Kingella kingae* | Fair Lawn | – | – |
| *Klebsiella pneumonias* | CMCC | – | – |
| *Pseudomonas aeruginosa* | CMCC | – | – |
| *Salmonella typhimurium* | CMCC | – | – |
| *Serratia marcescens* | CMCC | – | – |
| *Staphylococcus aureus* | CMCC | – | – |
| *Streptococcus pyogenes* | CMCC | – | – |

TABLE 2

| | Endocervical Swabs | |
|---|---|---|
| | Culture | |
| | + | – |
| *N. gonorrhoeae* | | |
| CoAmp + | 30 | 26 |
| CoAmp – | 7 | 404 |
| *C. trachomatis* | | |
| CoAmp + | 22 | 44 |
| CoAmp – | 12 | 391 |

TABLE 3

| | Urine Specimens | |
|---|---|---|
| | Culture | |
| | + | – |
| *N. gonorrhoeae* | | |
| CoAmp + | 124 | 50 |
| CoAmp – | 35 | 284 |
| *C. trachomatis* | | |
| CoAmp + | 32 | 49 |
| CoAmp – | 14 | 395 |

TABLE 4

POSITIVE REACTIONS ON SS06-T5 PROBE USING HYBRIZATION BUFFER

| # of PCR RUNS | # of PCRs TOTAL | CONTAINING 2.5M NaSCN | | CONTAINING 4.0M NaSCN | | HYB. ASSAY ON |
|---|---|---|---|---|---|---|
| | | # of + REACTIONS (Frequency) | A450 (nm) | # of + REACTIONS (Frequency) | A450 (nm) | ALTERNATIVE PROBE SS08 A450 |
| 1 | 285 | 2 (0.70%) | 2.421* | 0 (<0.3%) | 0.229 | NOT DONE |
| | | | 2.416* | | 0.246 | NOT DONE |
| 2 | 285 | 5 (1.75%) | 0.541 | 4 (1.40%) | 0.307 | 0.075 |
| | | | 0.571 | | 0.060 | 0.086 |
| | | | 0.366 | | 0.350 | 0.059 |
| | | | 0.726 | | 0.365 | 0.134 |
| | | | 0.432 | | 0.414 | 0.063 |
| 3 | 940 | 13 (1.38%) | 1.495** | 9 (0.96%) | 0.970 | 0.281 |
| | | | 1.219** | | 0.915 | 0.156 |
| | | | 3.727** | | 3.253 | 1.026 |
| | | | 0.330 | | 0.130 | 0.048 |

TABLE 4-continued

| | | POSITIVE REACTIONS ON SS06-T5 PROBE USING HYBRIZATION BUFFER | | | | |
|---|---|---|---|---|---|---|
| | | CONTAINING 2.5M NaSCN | | CONTAINING 4.0M NaSCN | | HYB. ASSAY ON |
| # of PCR RUNS | # of PCRs TOTAL | # of + REACTIONS (Frequency) | A450 (nm) | # of + REACTIONS (Frequency) | A450 (nm) | ALTERNATIVE PROBE SS08 A450 |
| | | | 1.578** | | 1.381 | 0.340 |
| | | | 0.266 | | 0.068 | 0.048 |
| | | | 2.491** | | 2.179 | 0.613 |
| | | | 2.257* | | 0.326 | 0.065 |
| | | | 3.406** | | 3.542 | 1.939 |
| | | | 3.157** | | 2.308 | 0.307 |
| | | | 3.242* | | 0.463 | 0.083 |
| | | | 0.598 | | 0.101 | 0.051 |
| | | | 2.294* | | 0.249 | 0.063 |
| 4 | 940 | 11 (1.17%) | 2.173** | 5 (0.53%) | 1.940 | 0.214 |
| | | | 0.893* | | 0.178 | 0.052 |
| | | | 0.740 | | 0.538 | 0.083 |
| | | | 2.452** | | 2.782 | 0.386 |
| | | | 0.506 | | 0.502 | 0.094 |
| | | | 0.329 | | 0.054 | 0.054 |
| | | | 0.267 | | 0.089 | 0.052 |
| | | | 0.357 | | 0.166 | 0.051 |
| | | | 0.379 | | 0.074 | 0.083 |
| | | | 0.349 | | 0.056 | 0.065 |
| | | | 1.256** | | 1.270 | 0.098 |
| 5 | 644 | 7 (1.08%) | 1.954* | 5 (0.77%) | 0.335 | NOT DONE |
| | | | 0.551 | | 0.503 | NOT DONE |
| | | | 2.759* | | 0.508 | 0.061 |
| | | | 2.601* | | 0.555 | NOT DONE |
| | | | 3.510* | | 0.591 | 0.065 |
| | | | 2.389* | | 0.219 | NOT DONE |
| | | | 0.964 | | 0,158 | NOT DONE |

We claim:

1. A method for determining the presence or absence of *N. gonorrhoeae* and/or *C. trachomatis* in a fluid sample suspected of containing either or both *N. gonorrhoeae* and *C. trachomatis* comprising:

(a) treating said sample with an aqueous solution containing at least four oligonucleotide primers, two of said primers being capable of hybridizing selectively with the two complementary strands of *N. gonorrhoeae* DNA which contain the target sequence, said primers having SEQ ID NO: 1 and SEQ ID NO:2, respectively, and the other two primers being capable of hybridizing selectively with the two complementary strands of *C. trachomatis* DNA which contain the target sequence, said primers having SEQ ID NO:4 and SEQ ID NO:5, respectively, said aqueous solution also containing an inert organic polar solvent as a cosolvent;

(b) synthesizing an extension product of each of said primers, which extension product(s) containing the target DNA sequence(s), and amplifying said target sequences(s) if present;

(c) treating said sample, after the intended amplification(s), with two oligonucleotide probes: one probe having sequence SEQ ID NO:3 which is uniquely complementary to a sequence in the amplified region of *N. gonorrhoeae*, and a second probe having sequence SEQ ID NO:6 which is uniquely complementary to a sequence in the amplified region of *C. trachomatis*;

(d) incubating the amplified target region(s), if any, with each of the oligonucleotide probes, under stringent conditions, and allowing for hybridization between each of said probes and the target region for said probe; and (e) detecting hybrids formed between the amplified target regions(s), if any, and the oligonucleotide probe(s).

2. The method of claim 1, wherein Step (d) is carried out in the presence of a buffer.

3. The method of claim 2 wherein the buffer comprises NaSCN at a concentration of about 4.0M.

4. A PCR kit for the detection of either or both *N. gonorrhoeae* and *C. trachomatis*, comprising a container having an aqueous solution which includes oligonucleotide primers having sequences SEQ ID NO:1, SEQ ID NO:2, SEQ ID NO:4 and SEQ ID NO:5, said aqueous solution further containing as a cosolvent an organic polar solvent; and separate from said container, an oligonucleotide probe for *N. gonorrhoeae* having sequence SEQ ID NO:3 and a probe for *C. trachomatis* having the sequence SEQ ID NO:6.

5. The kit of claim 4 wherein the probes are immobilized on a microtiter plate.

6. The kit of claim 5 wherein the oligonucleotide primers are labeled.

7. The kit of claim 6 wherein the primers are labeled with biotin.

8. The kit of claim 4 wherein said cosolvent is present in an amount of from about 1% to about 20% by volume of said solution.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Neisseria gonorrheae ( x i ) SEQUENCE DESCRIPTION: SEQ ID NO:1:

TAGCCACGTT TATCGTCGTA TGC    23

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single

```
             ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:
```

AACAGCATTA CCAATCTGGC GAC 23

( 2 ) INFORMATION FOR SEQ ID NO:3:

```
         ( i ) SEQUENCE CHARACTERISTICS:
                 ( A ) LENGTH: 20 base pairs
                 ( B ) TYPE: nucleic acid
                 ( C ) STRANDEDNESS: single
                 ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:
```

GCGGTTCAGG GAAGTGATAG 20

( 2 ) INFORMATION FOR SEQ ID NO:4:

```
         ( i ) SEQUENCE CHARACTERISTICS:
                 ( A ) LENGTH: 25 base pairs
                 ( B ) TYPE: nucleic acid
                 ( C ) STRANDEDNESS: single
                 ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:
```

GGGATTCCTG TAACAACAAG TCAGG 25

( 2 ) INFORMATION FOR SEQ ID NO:5:

```
         ( i ) SEQUENCE CHARACTERISTICS:
                 ( A ) LENGTH: 26 base pairs
                 ( B ) TYPE: nucleic acid
                 ( C ) STRANDEDNESS: single
                 ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:
```

CCTCTTCCCC AGAACAATAA GAACAC 26

( 2 ) INFORMATION FOR SEQ ID NO:6:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:6:

CATAGCACTA TAGAACTCTG CAAGCC                                          26

(2) INFORMATION FOR SEQ ID NO:7:

(i) SEQUENCE CHARACTERISTICS:
    (A) LENGTH: 202 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:7:

TAGCCACGTT TATCGTCGTA TGCATCGGAA CGAGCCATCA AAAACAATTA TTGCAGCAGG      60

TGGCGGTGGT ACTTGGGGCT ATCACTTCCC TGAACCGCGT GCTTTTACTA ATAGAGAACG     120

AGCAAGGCTT CAAAGTTTTC CTGATGATTT TGAGTTTGTC GGATCAACAA CTGAAGTACG    180

TCGCCAGATT GGTAATGCTG TT                                             202